US011771455B2

(12) United States Patent
Gregan et al.

(10) Patent No.: US 11,771,455 B2
(45) Date of Patent: Oct. 3, 2023

(54) ENDOSCOPIC RESECTION ASSEMBLY

(71) Applicant: UNITED STATES ENDOSCOPY GROUP, INC., Mentor, OH (US)

(72) Inventors: Darren Gregan, Auburn Township, OH (US); Jessica Russo, Sagamore Hills, OH (US); Seth Byers, Mentor, OH (US); Reza Mohammadpour, Willoughby Hills, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 197 days.

(21) Appl. No.: 17/497,677

(22) Filed: Oct. 8, 2021

(65) Prior Publication Data

US 2022/0110652 A1  Apr. 14, 2022

Related U.S. Application Data

(60) Provisional application No. 63/089,360, filed on Oct. 8, 2020.

(51) Int. Cl.
*A61B 17/32* (2006.01)
*A61B 17/00* (2006.01)

(52) U.S. Cl.
CPC .. *A61B 17/320016* (2013.01); *A61B 17/0057* (2013.01); *A61B 2017/00584* (2013.01)

(58) Field of Classification Search
CPC ............. A61B 1/00087; A61B 1/0014; A61B 17/0057; A61B 17/1227; A61B 17/1285; A61B 17/320016; A61B 17/32056; A61B 2017/00269; A61B 2017/00296; A61B 2017/00477; A61B 2017/00584; A61B 2017/00845; A61B 2017/00907; A61B 2017/306; A61B 2090/037
See application file for complete search history.

(56) References Cited

U.S. PATENT DOCUMENTS

| 5,968,056 A * | 10/1999 | Chu ........................ A61B 18/14 606/139 |
| 2012/0010633 A1 | 1/2012 | Noda et al. |
| 2013/0172918 A1 | 7/2013 | Smith et al. |
| 2014/0100423 A1 | 4/2014 | Monassevitch et al. |
| 2015/0230782 A1 | 8/2015 | Labombard |

OTHER PUBLICATIONS

International Search Report from PCT/US2021/054266 dated Jan. 19, 2022.

* cited by examiner

*Primary Examiner* — Mohamed G Gabr
(74) *Attorney, Agent, or Firm* — Calfee, Halter & Griswold LLP (57) ABSTRACT

An endoscopic resection assembly includes an adaptor configured to adapt to an endoscopic device. A pusher is disposed on the adaptor by inserting the adaptor into the central opening defined by the pusher. A cutting device includes a snare loop and a snare drive cable, and is removably coupled to the pusher. The cutting device is configured to resect a tissue when the snare loop is contracted by activation of the snare driver. A clip for engaging onto the tissue can be loaded onto the adaptor at a position distal to the pusher.

13 Claims, 8 Drawing Sheets

ENDOSCOPIC RESECTION ASSEMBLY

CROSS-REFERENCE TO RELATED APPLICATION

This application claims the benefit of priority to U.S. Provisional App. No. 63/089,360, filed on Oct. 8, 2020, which is incorporated herein by reference in its entirety.

FIELD OF THE INVENTION

The present application is directed to devices used in surgical procedures, such as endoscopic procedures, and more particularly to endoscopic resection assemblies that can be connected to an endoscopic device.

BACKGROUND

Endoscopic resection procedures, such as diagnostic tissue acquisition from the digestive tract, may be performed with an endoscope and an endoscopic resection device. In general, an endoscope includes a long flexible insertion tube having one or more channels through which miniaturized, flexible instruments can be inserted and advanced. The endoscope typically includes various optical features allowing for visualization of internal views of particular body parts, organs, or passages without requiring invasive surgery. For example, the insertion tube may transmit images or image-producing signals from the illuminated operative site to a viewing means, providing the operator with full vision of the actions being performed at the working end of the endoscope.

In some endoscopic full thickness resection procedures, the operator first identifies a tissue such as a lesion in the digestive tract. The tissue is pulled into a cap provided on the endoscopic device via suction or other means. Next, a clip is deployed over the tissue. Lastly, a cutting device such as a snare cuts over the top of the clip, removing the tissue and leaving the clip closed over the otherwise open defect.

The clip should be deployed before the cutting in order to pre-close the defect resulting from the cutting. Also, the clip should remain at the resection site until the body can heal itself. Therefore, there is a need for preventing the cutting of the tissue before the clip is deployed. There is also a need for ensuring that some tissue remain on top of the clip after resection and removal of the tissue, such that the clip can remain locked onto the resection site.

SUMMARY OF THE INVENTION

Embodiments of the present invention provide endoscopic resection assemblies for use in endoscopic procedures. The inventive endoscopic resection assemblies can be designed and shaped to function with endoscopic devices generally or may be designed and shaped to function with endoscopic devices having a particular structure unique to a single manufacturer of endoscopic devices.

In one aspect of the subject matter, the endoscopic resection assembly includes an adaptor configured to couple to an endoscopic device. A pusher is disposed on the adaptor. At least one driver is configured to move the pusher in a distal direction with respect to the adaptor. A cutting device is removably coupled to the pusher, and is configured to be removed from the pusher when at least a portion of the pusher is distal to the adapter. The adaptor is configured to be loaded with a clip. The clip is released from the adaptor and engages onto a tissue before the cutting device is removed from the pusher.

Further features and advantages of the invention will become apparent from the following detailed description made with reference to the accompanying drawings.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", and "the", include plural referents unless the context clearly dictates otherwise.

Embodiments of the present invention can be used for cutting into or through the muscularis of the GI tract in order to remove dysplasia that has invaded past the mucosal layer of tissue. A clip can be deployed over the tissue prior to resection in order to pre-close the resulting defect created from the resection.

Figure 5A:
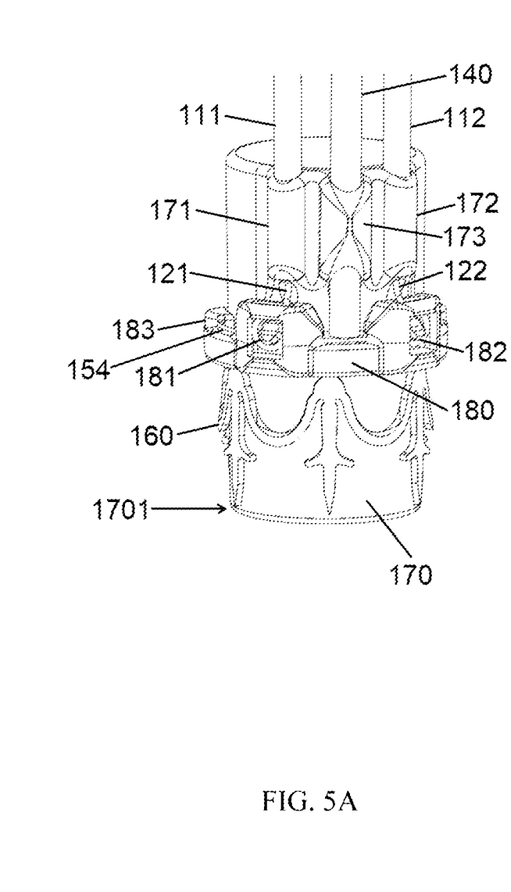
FIG. 5A is a perspective view of the assembly of a pusher and a clip with an adaptor according to an exemplary embodiment.
Figure 5B:
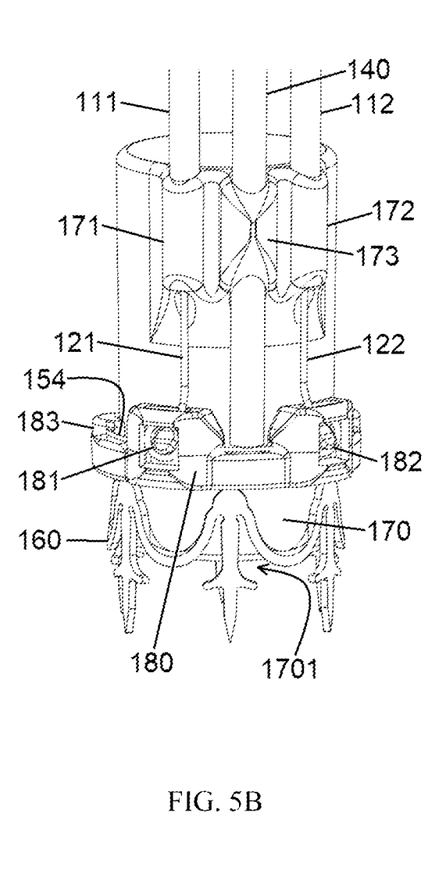
FIG. 5B is a perspective view of the assembly of a pusher and a clip with an adaptor during a resection operation according to an exemplary embodiment.
Figure 5C:
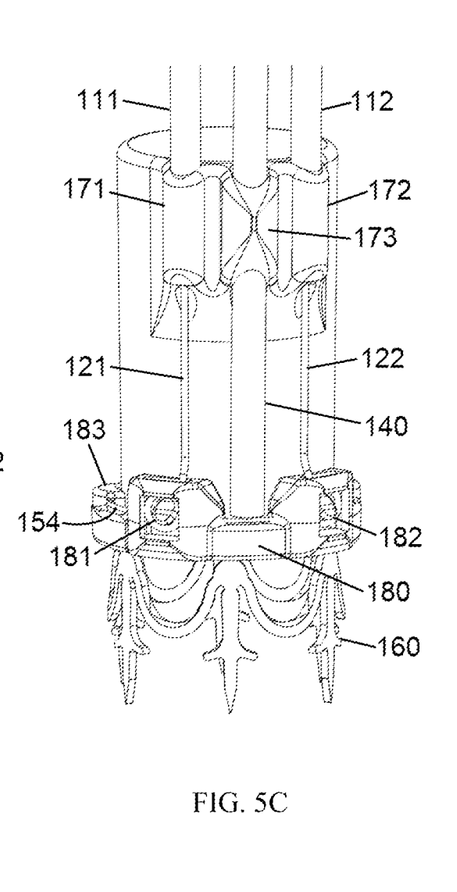
FIG. 5C is a perspective view of the assembly of a pusher and a clip with an adaptor during a resection operation according to an exemplary embodiment.
Figure 6A:
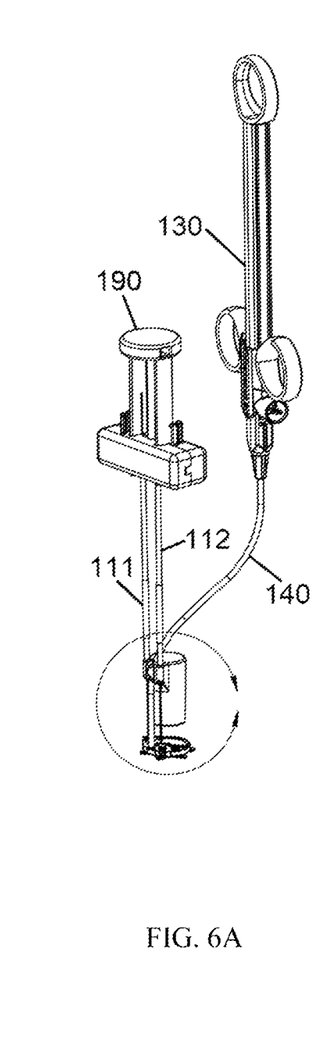
FIG. 6A is a perspective view of the overall assembly of an endoscopic resection assembly in a deployed position according to an exemplary embodiment.
Figure 6B:
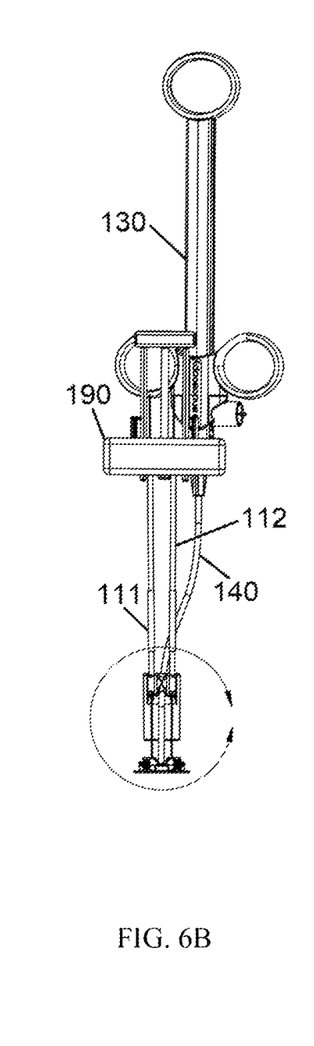
FIG. 6B is a front view of the overall assembly of an endoscopic resection assembly in a deployed position according to an exemplary embodiment.
Figure 6C:
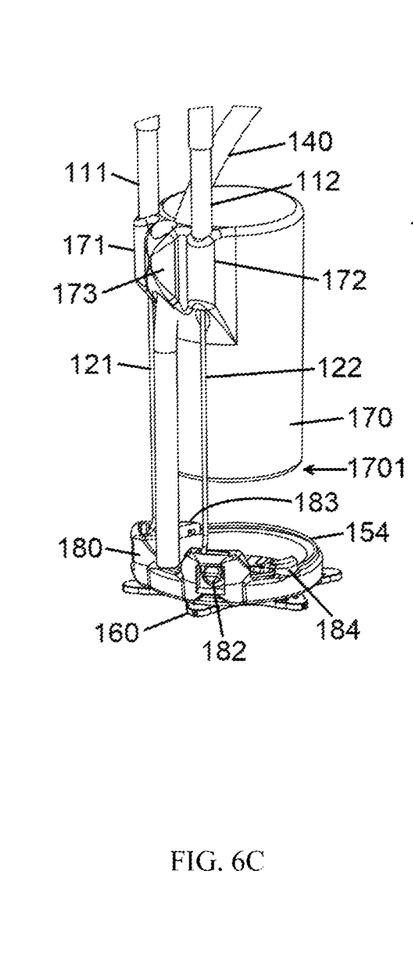
FIG. 6C is an enlarged view of an adaptor, a pusher, a clip, a cutting device, a catheter, a first sheath, a second sheath, a first driver, and a second driver in a deployed position shown in FIG. 6A.
Figure 6D:
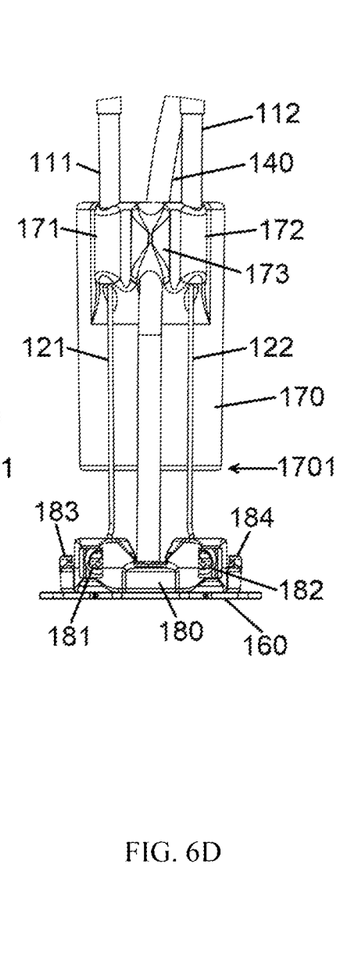
FIG. 6D is an enlarged view of an adaptor, a pusher, a clip, a cutting device, a catheter, a first sheath, a second sheath, a first driver, and a second driver in a deployed position according to an exemplary embodiment shown in FIG. 6B.

As illustrated in FIGS. 1A-1C and 2A-2C, in some embodiments, an endoscopic resection assembly 100 includes an adaptor 170, a pusher 180, a cutting device 150, and a clip 160. The adaptor 170 is configured to attach to an endoscopic device. As illustrated in FIGS. 5A-5C, the pusher 180 is disposed on the adaptor 170 and configured to slide in the axial direction with respect to the adaptor 170. The cutting device 150 is an endoscopic tool for cutting a tissue, which operates between an open state and a closed state. As illustrated in FIGS. 3A and 3B, the cutting device 150 is removably coupled to the pusher 180. The clip 160 is an endoscopic tool configured to operate between an open state and a closed state, and is configured to engage onto a tissue. As illustrated in FIGS. 5A-5C, the clip 160 is loaded on the adaptor 170 in the open state at a position distal to the pusher 180. The endoscopic resection assembly 100 further includes at least one driver, controlled by an operator, configured to slide the pusher 180 in the distal direction with respect to the adaptor 170. As the pusher 180 slides in the distal direction with respect to the adaptor 170, the clip 160 is pushed by the pusher 180 to slide off the distal edge 1701 of the adaptor 170, and engages onto a tissue by reforming toward the closed state. The cutting device 150 can then be activated by the operator to detach from the pusher 180, and resect tissue above the pusher by operating toward the closed state.

As illustrated in FIGS. 1A-1C and 2A-2C, in some embodiments, the endoscopic resection assembly 100 includes at least one driver and at least one sheath, a catheter 140, a clip deployment handle 190, and a handle 130. In some embodiments, the at least one driver comprises a first driver 121 and a second driver 122. In some embodiments, the at least one sheath comprises a first sheath 111 and a second sheath 112. In some embodiments, the drivers may be directly adjacent to one another or spaced apart somewhat along the circumference of the pusher 180. For example, the drivers may be spaced about 10 degrees to 180 degrees, or about 15 degrees to 90 degrees, or about 30 degrees, apart from one another.

FIG. 3B illustrates the assembly of the distal components of the endoscopic resection assembly 100, including the pusher 180, the cutting device 150, and the at least one driver. The cutting device 150 is an endoscopic tool for cutting a tissue, and operates between an open state and a closed state. In some embodiments, the cutting device 150 has a snare drive cable 152 and a snare loop 154. In some embodiments, the pusher 180 includes at least one retainer. As illustrated in FIG. 3B, in some embodiments, the at least one retainer comprises the first retainer 183 and the second retainer 184, and retains the snare loop 154, such that the cutting device 150 is removably coupled to the pusher 180. The pusher 180 is driven by the at least one driver. As illustrated in FIG. 3B, in some embodiments, the at least one driver comprises the first driver 121 and the second driver 122. In some embodiments, the first driver 121 and the second driver 122 can be actuated to move the pusher 180 in the distal direction.

As illustrated in FIGS. 5A-5C, the pusher 180 is disposed on the adaptor 170 and configured to slide in the axial direction with respect to the adaptor 170. The adaptor 170 may comprise a material to reduce friction and support movement of the pusher 180 and the clip 160. Suitable materials for the adaptor 170 include plastics such as polycarbonate, K-resin, acrylic, xylar, ASA, polypropylene, silicone, and TPES, or other similar materials. The adaptor 170 may comprise such plastics, or other materials, entirely or in part. The clip 160 is an endoscopic tool configured to operate between an open state and a closed state, and is configured to engage onto a tissue. The clip 160 is loaded on the adaptor in the open state at a position distal to the pusher 180. In some embodiments, the pusher 180 and the clip 160 are not secured together. However, in some embodiments, the pusher 180 and the clip 160 are secured together. For example, one or more indents can be formed on the pusher 180, and one or more protrusions can be formed on the clip 160, where the one or more protrusions are configured to be secured into the one or more indents. The pusher 180 and the clip 160 can be secured together by other means such as welding, gluing, and overmolding. In some embodiments, the snare drive cable 152 of the cutting device 150 extends within the catheter 140. In some embodiments, the catheter 140 is coupled with the adaptor 170. In some embodiments, the at least one driver respectively extends within the at least one sheath. As illustrated in FIG. 2C, in some embodiments, the first driver 121 and the second driver 122 respectively extend within the first sheath 111 and the second sheath 112. In some embodiments, the at least one sheath can be attached to the adaptor 170.

In some embodiments, the at least one driver can be actuated to move the pusher 180 in the distal direction. As result, the pusher 180 slides in the distal direction with respect to the adaptor 170. In some embodiments, as the pusher 180 slides in the distal direction with respect to the adaptor 170, the clip 160 is pushed by the pusher to slide off the distal edge 1701 of the adaptor 170, and engage onto a tissue by reverting to the closed state. The cutting device 150 can be activated to detach from the pusher 180, and cut a tissue by operating toward the closed state.

Figure 1A:
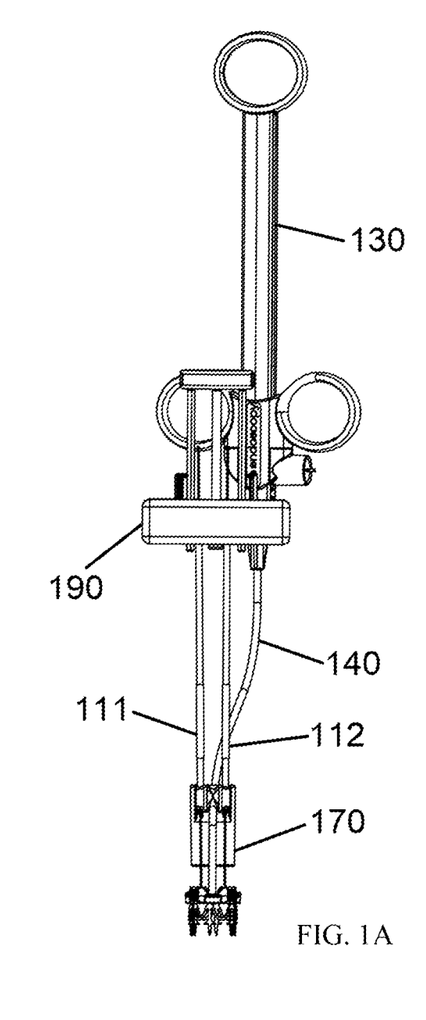
FIG. 1A is a front view of the overall assembly of an endoscopic resection assembly according to an exemplary embodiment.
Figure 1B:
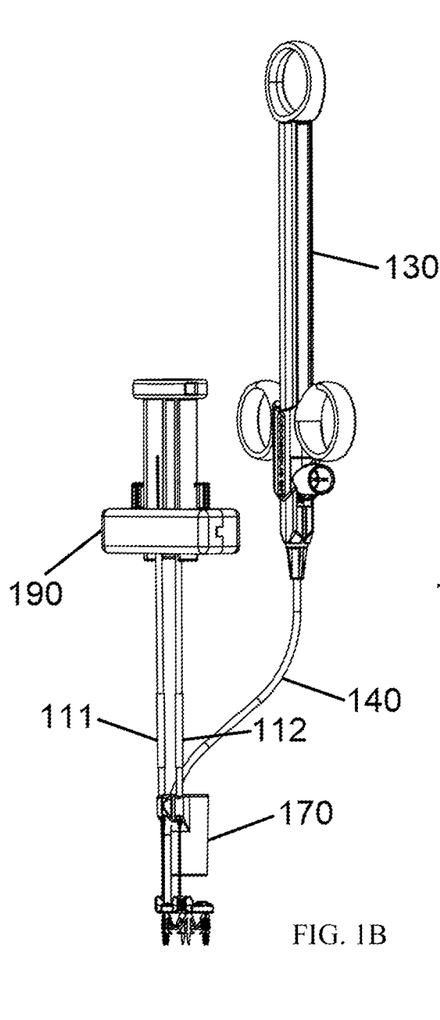
FIG. 1B is a side view of the overall assembly shown in FIG. 1A.
Figure 1C:
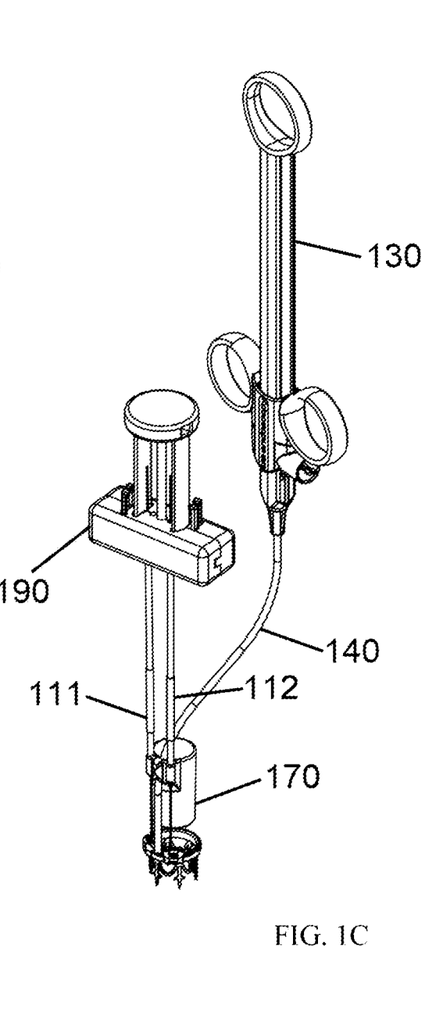
FIG. 1C is a perspective view of the overall assembly shown in FIG. 1A.
Figure 2A:
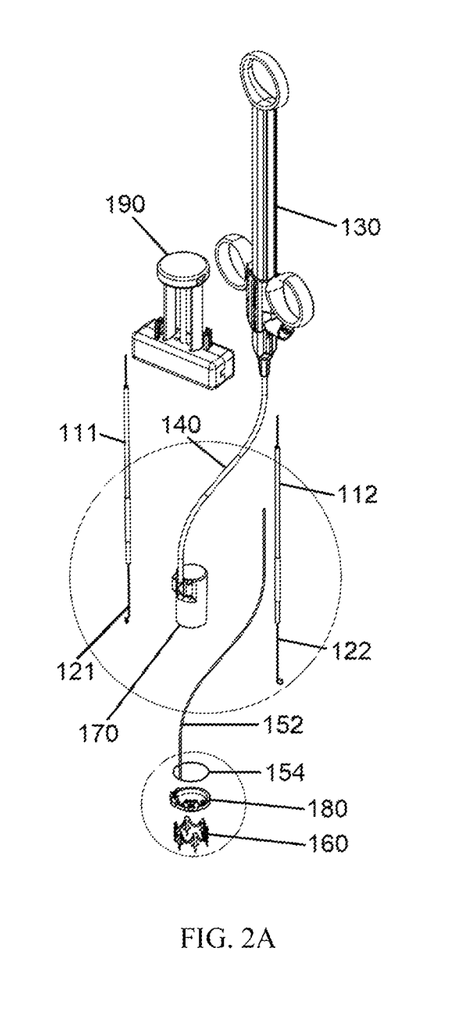
FIG. 2A is an exploded view of an endoscopic resection assembly shown in FIGS. 1A-1C.
Figure 2B:
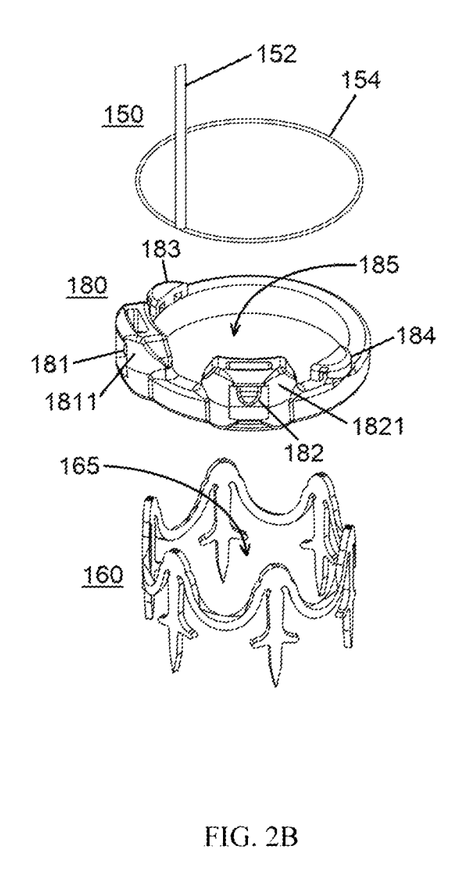
FIG. 2B is an enlarged view of a cutting device, a pusher, and a clip shown in FIG. 2A.
Figure 2C:
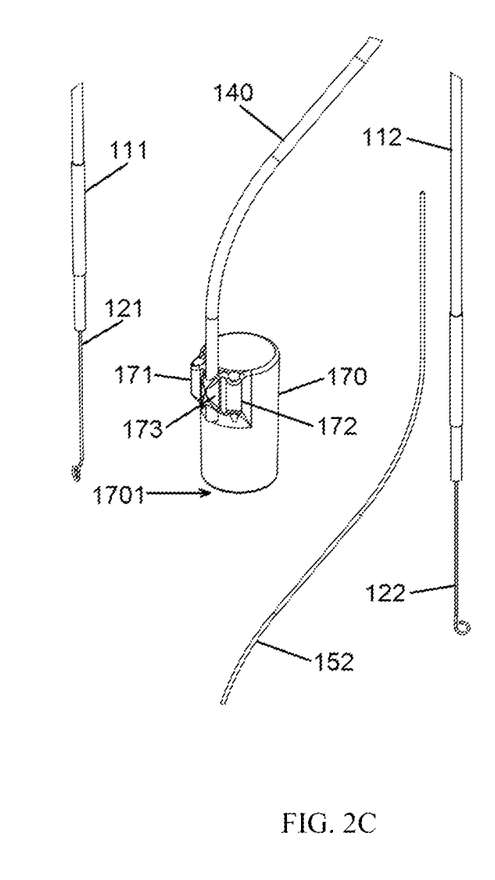
FIG. 2C is an enlarged view of a first sheath, a second sheath, a first driver, a second driver, a snare drive cable, an adaptor, and a catheter shown in FIG. 2A.
Figure 3A:
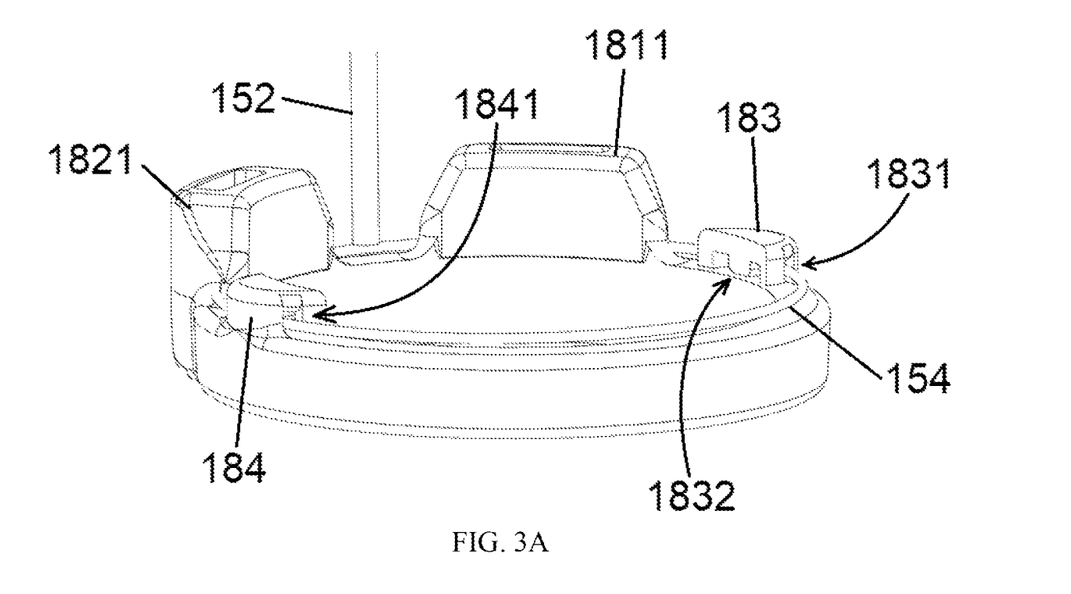
FIG. 3A is a perspective view of the assembly of a pusher and a cutting device according to an exemplary embodiment.
Figure 3B:
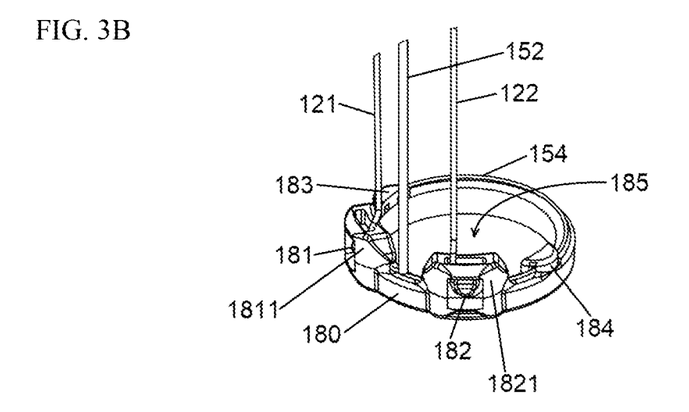
FIG. 3B is a perspective view of the assembly of a pusher, a cutting device, a first driver, and a second driver according to an exemplary embodiment.

As illustrated in FIGS. 2A and 2C, the adaptor 170 has an inside surface and an outside surface. In some embodiments, the adaptor 170 includes a lumen 173 and at least one overmolding. As illustrated in FIGS. 2A and 2C, the at least one overmolding may comprise an overmolding 171 and an overmolding 172.

In some embodiments, the adaptor 170 is substantially tubular with a distal open end and a proximal open end. The adaptor 170 is hollow and defines a tissue chamber channel. In various embodiments, the adaptor 170 is configured to attach with different types of endoscopic devices (e.g., Olympus®, Fujinon®, or Pentax® endoscopes). For example, the inner and outer surface of the adaptor 170 may be contoured, and the inner and outer diameter of the adaptor 170 may be varied, in order to provide a good fit with the endoscopic device. In some embodiments, the endoscopic device is press-fitted to the proximal end of the adaptor 170. Flexible materials, such as rubber and other elastic polymers, can be overmolded or glued on the inside surface of the adaptor 170 in order to strengthen the fitting of the endoscopic device and the adaptor 170. In some embodiments, the adaptor 170 comprises a flexible band, such as a rubber band, configured to be wrapped around the distal end of the endoscopic device. A person skilled in the art should understand that the shape of the adaptor 170 or the shape the tissue chamber channel can be any suitable shapes as long as it does not interfere with the operations of the endoscopic device. The tissue chamber channel is configured to receive the tissue to be resected during resection operation. In some embodiments, the adaptor 170 is entirely or partially formed with materials sufficiently transparent to allow visualization of outside environment through various optical features from the inside of the adaptor 170. In some embodiments, during resection operation, the sufficiently transparent materials can allow the operator to confirm whether the clip 160 is deployed, and observe the position of the cutting device 150 prior to tissue resection.

The adaptor 170 is configured to allow the clip 160 and the pusher 180 to be disposed on the adaptor 170. In some embodiments, as illustrated in FIGS. 5A-5C, the adaptor 170 is configured to allow the clip 160 and the pusher 180 to be disposed on the outside surface of the adaptor 170. The adaptor 170 is configured to allow the clip 160 and the pusher 180 to slide in the axial direction with respect to the adaptor 170. In some embodiments, as illustrated in FIGS. 5A-5C, the outside surface of the adaptor 170 is a smooth surface such that the clip 160 and the pusher 180 can slide in the axial direction with respect to the adaptor 170.

A person skilled in the art should understand that the adaptor 170 may have any shape and may include any structural components, as long as the clip 160 and the pusher 180 can be disposed on the adaptor 170 and slide in the axial direction with respect to the adaptor 170. For example, in some embodiments, the adaptor 170 is configured to allow the clip 160 and/or the pusher 180 to be disposed on the inside surface of the adaptor 170. In some embodiments, the adaptor 170 includes a support surface formed inside the adaptor 170, such that the clip 160 and/or the pusher 180 can be disposed on the support surface. In some embodiments, the adaptor 170 can include one or more guide rails, such that the clip 160 and/or the pusher 180 are allowed to slide in the axial direction along the one or more guide rails. In some embodiments, the adaptor 170 includes one or more longitudinal slits, such that the clip 160 and/or the pusher 180 are allowed to slide in the axial direction along the one or more longitudinal slits.

In some embodiments, the adaptor 170 may be configured to couple with the catheter 140. As illustrated in FIG. 2C, in some embodiments, the adaptor 170 is coupled with the catheter 140 by inserting the catheter 140 into the lumen 173 of the adaptor 170. The lumen 173 may be formed on the outside surface of the adaptor 170, such that the catheter 140 is coupled with the outside surface of the adaptor 170. The lumen 173 may provide slip fit between the catheter 140 and the adaptor 170, such that the catheter 140 is allowed to freely slide in the axial direction with respect to the adaptor 170. A person skilled in the art should understand that the catheter 140 may be coupled to any portion of the adaptor 170, such as the inside surface of the adaptor 170, as long as the catheter 140 does not interfere with the operations of the endoscopic device and other components of the endoscopic resection assembly 100. In some embodiments, the catheter 140 may penetrate the adaptor 170, such that the catheter 140 extends through a hole formed on the adaptor 170. In addition, a person skilled in the art should understand that the adaptor 170 can be fixed with the catheter 140, or be detached from the catheter 140, as long as the catheter 140 does not interfere with the operations of the endoscopic device and other components of the endoscopic resection assembly 100.

In some embodiments, the adaptor 170 may be configured to attach with the at least one sheath. As illustrated in FIGS. 5A-5C, in some embodiments, the at least one sheath comprises the first sheath 111 and the second sheath 112, and the first sheath 111 and the second sheath 112 are attached to the adaptor 170 respectively by the overmolding 171 and the overmolding 172. In some embodiments, the overmolding 171 and the overmolding 172 are formed on the outside surface of the adaptor 170, such that the at least one sheath is attached to the outside surface of the adaptor 170. A person skilled in the art should understand that the at least one sheath can be attached with the adaptor 170 by other means, for example, friction, heat staking, gluing, or welding. A person skilled in the art should also understand that the at least one sheath can be attached to any portion of the adaptor 170, such as the inside surface of the adaptor 170, as long as the at least one sheath does not interfere with the operations of the endoscopic device and other components of the endoscopic resection assembly 100. In some embodiments, the at least one sheath may penetrate the adaptor 170, such that the at least one sheath extends through a hole formed on the adaptor 170. In addition, a person skilled in the art should understand that the at least one sheath may not be attached with the adaptor 170. Instead, the at least one sheath may be attached with any component of the endoscopic device or the endoscopic resection assembly 100, as long as the at least one sheath does not interfere with the operations of the endoscopic device and other components of the endoscopic resection assembly 100.

As illustrated in FIG. 2B, in some embodiments, the pusher 180 includes at least one knob which comprises the first knob 181 and the second knob 182, and at least one retainer which comprises the first retainer 183 and the second retainer 184.

The pusher 180 is configured to be disposed on the adaptor 170 and can slide in the axial direction with respect to the adaptor 170. As illustrated in FIG. 2B, in some embodiments, the pusher 180 is substantially ring-shaped, defining a central opening 185. As illustrated in FIG. 5A, in some embodiments, the adaptor can be inserted into the central opening 185, such that the pusher 180 is disposed on the outside surface of the adaptor 170 and can slide in the axial direction with respect to the adaptor 170. In various embodiments, the central opening 185 may have different shapes to fit with the different shapes of the outside surface of the adaptor 170. In various embodiments, the pusher 180 may be configured to be disposed on the inside surface or the outside surface of the adaptor 170, or on a support surface formed inside the adaptor 170. In various embodiments, the pusher 180 may include structural components, such as protrusions and indents, to fit with guide rails, longitudinal slits, or other structural components of the adaptor 170, such that the pusher 180 can slide in the axial direction with respect to the adaptor 170.

In some embodiments, the pusher 180 has a closed ring structure configured to be disposed on the entire periphery of the adaptor 170, as illustrated in FIG. 5A. A person skilled in the art should understand that the pusher 180 may be disposed on a portion of the periphery of the adaptor 170, as long as there is no interference with the operations of the endoscopic device and other components of the endoscopic resection assembly 100. For example, the pusher 180 may have a half-ring structure configured to be disposed on a half of the periphery of the adaptor 170.

In some embodiments, the pusher 180 is attached with at least one driver. The pusher 180 may include at least one knob for attaching with the at least one driver. In some embodiments, as illustrated in FIGS. 2B and 2C, the at least one driver comprises a first driver 121 and a second driver 122, and the at least one knob comprises the first knob 181 and the second knob 182. In some embodiments, as illustrated in FIGS. 2C and 3B, the distal ends of the first driver 121 and the second driver 122 are bent into a circle and fitted around the first knob 181 and the second knob 182. As such, the at least one driver is secured to the at least one knob of the pusher 180. In some embodiments, the at least one knob is a round knob over which the bent distal end of the at least one driver can be snapped into place. A person skilled in the art should understand that the at least one driver may fit with, or be secured to, other structural components of the pusher 180, for example, one or more holes formed on the pusher 180. Glue may be applied to reinforce the attachment of the at least one driver to the pusher 180. In various embodiments, the at least one driver may be attached to the pusher 180 by different means, for example, gluing, welding, or overmolding.

The at least one driver is configured to move the pusher 180 in the distal direction. In some embodiments, as illustrated in FIGS. 5A-5C, the first driver 121 and the second driver 122 respectively extend within the first sheath 111 and the second sheath 112. In some embodiments, the first driver 121 and the second driver 122 can be actuated to advance in the distal direction with respect to the first sheath 111 and the second sheath 112, pushing the pusher 180 in the distal direction. A person skilled in the art should understand that the at least one driver may comprise various structural components configured to move the pusher 180 in the distal direction. For example, in some embodiments, the at least one driver can comprise a pull thread with a distal end tied on the pusher 180, where the pull thread is configured to pull the pusher 180 in the distal direction when a proximal end of the pull thread is retracted. A person skilled in the art should also understand that the at least one driver may not be coupled or attached to the pusher 180, as long as the pusher 180 can be driven by the at least one driver in the distal direction.

In some embodiments, a spring is coupled to the clip deployment handle 190 or the at least one sheath. The spring can be configured to be compressed or extended, such that the spring exerts a force on the at least one driver in the axial direction. The clip deployment handle 190 can include a stopper for preventing the axial movement of the at least one driver with respect to the at least one sheath. The clip deployment handle 190 can be configured to activate the stopper by, for example, deforming the stopper, such that the stopper no longer prevents the axial movement of the at least one driver. As result, the compressed or extended spring moves the at least one driver in the axial direction with respect to the at least one sheath, and the at least one driver moves the pusher 180 in the distal direction.

In some embodiments, the pusher 180 is spring loaded on the adaptor 170. A spring can be coupled with the adaptor 170 and configured to be compressed or extended by the pusher 180 when the pusher 180 is disposed on the adaptor 170. As such, the spring exerts a force on the pusher 180 in the distal direction. A stopper can be coupled to the adaptor 170, the endoscopic device, or other structural components of the endoscopic resection assembly 100, and can be configured to prevent the distal movement of the pusher 180 with respect to the adaptor 170. An actuator, such as a pull thread extending within a sheath, can be operatively coupled with the stopper. The actuator is configured to activate the stopper by, for example, deforming the stopper or detaching the stopper from other structural components, such that the stopper no longer prevents the distal movement of the pusher 180. As result, the compressed spring pushes the pusher 180, and the pusher 180 slides in the distal direction with respect to the adaptor 170.

In some embodiments, the adaptor 170 is slidably coupled with the endoscopic device, such that the adaptor 170 can slide in the axial direction with respect to the endoscopic device. An actuator, such as a pull thread extending within a sheath, can be operatively coupled with the adaptor. The actuator is configured to move the adaptor 170 in the proximal direction with respect to the endoscopic device and the pusher 180, such that the pusher 180 moves in the distal direction in relative to the adaptor 170.

The pusher 180 is removably coupled with the cutting device 150. The cutting device 150 is an endoscopic tool for cutting a tissue, which operates between an open state and a closed state. In some embodiments, as illustrated in FIG. 2B, the cutting device 150 includes a snare drive cable 152 and a snare loop 154. FIG. 2B illustrates the cutting device 150 in the open state. The snare drive cable 152 can be actuated to contract the snare loop 154, such that the cutting device 150 operates toward the closed state.

Figure 2D:
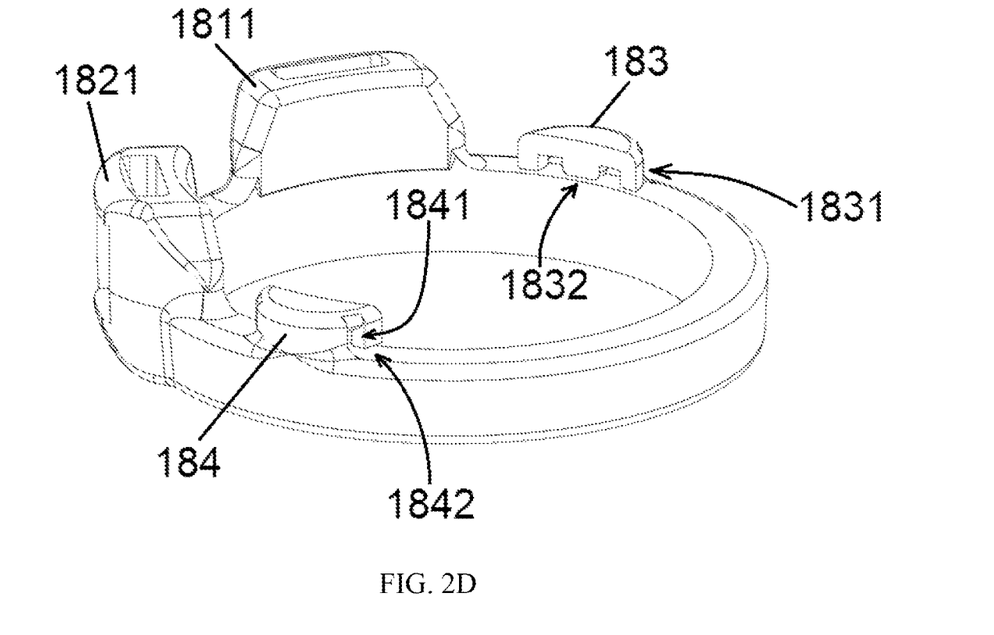
FIG. 2D is a perspective view of a pusher according to an exemplary embodiment.

In some embodiments, the pusher 180 includes at least one retainer. As illustrated in FIGS. 2D and 3A, in some embodiments, the at least one retainer comprises the first retainer 183 and the second retainer 184. In some embodiments, each of the at least one retainer defines a passage and a slit. As illustrated in FIGS. 2D and 3A, the first retainer 183 defines a passage 1831 and a slit 1832, and the second retainer 184 defines a passage 1841 and a slit 1842. In some embodiments, the passage defined by the at least one retainer is configured to accommodate the snare loop 154 of the cutting device 150. In some embodiments, the slit defined by the at least one retainer is configured to communicate the passage with the central opening 185 defined by the pusher 180. FIG. 3B illustrates the assembly of the cutting device 150 with the pusher 180. As illustrated in FIG. 3B, the snare loop 154 is in the open state and accommodated in the passage 1831 defined by the first retainer 183 and the passage 1841 defined by the second retainer 184. As such, the snare loop 154 lies in a plane substantially parallel to the plane defined by the pusher 180, and moves in tandem with the pusher 180 when the pusher 180 moves in the axial direction. When the snare loop 154 is contracted by actuating the snare drive cable 152, the slit 1832 defined by the first retainer 183 and the slit 1842 defined by the second retainer 184 allow the snare loop 154 to escape from the passage and move radially inward into the central opening 185 defined by the pusher 180. The pusher 180 can be formed from one or more components that could be snapped, glued, or welded together to form the at least one retainer that removably retains the cutting device 150 to the pusher 180.

Figure 3C:
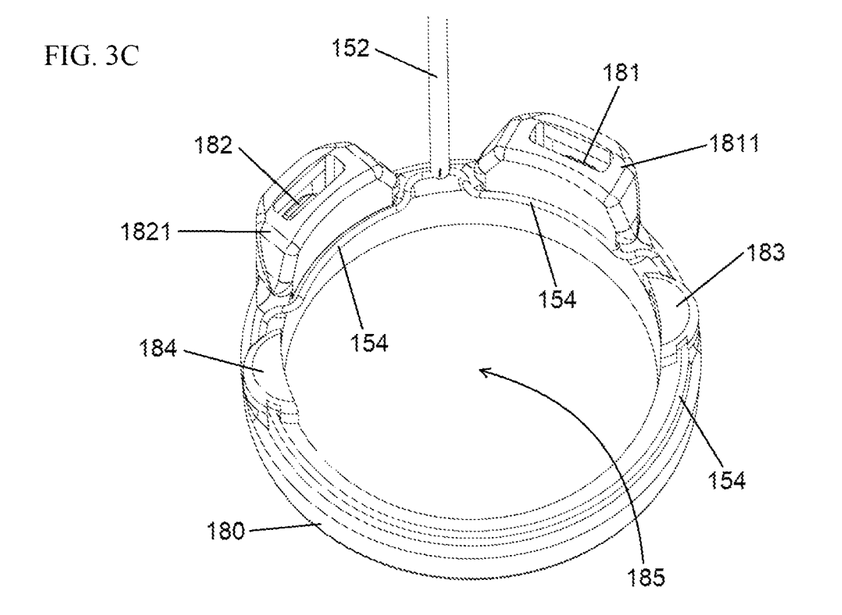
FIG. 3C is a perspective view of the assembly of a pusher and a cutting device according to an exemplary embodiment.

In some embodiments, the pusher 180 includes at least one housing formed around the at least one knob. As illustrated in FIG. 3C, a housing 1811 can be formed around the knob 181 and a housing 1821 can be formed around the knob 182. As illustrated in FIG. 3C, in some embodiments, the snare loop 154 is bent at the positions where the at least one housing is located, such that the snare loop 154 is positioned along the inward facing surface of the at least one housing. As such, the at least one housing does not block the operation of the snare loop 154 between the open state and the closed state. A person skilled in the art should understand that in any embodiment, the snare loop 154 can be bent or deformed to extend around various structural components formed on the pusher 180, such that the structural components do not block the operation of the snare loop 154 between the open state and the closed state. A person skilled in the art should also understand that in any embodiment, passages for accommodating the snare loop 154 can be formed on the surface of the various structural components of the pusher 180, such that the structural components do not block the operation of the snare loop 154 between the open state and the closed state.

As illustrated in FIGS. 2D and 3A, in some embodiments, the at least one retainer is formed on the proximal surface of the pusher 180. As such, when the snare loop 154 is accommodated in the passage formed through the at least one retainer, the snare loop 154 is positioned at a set distance from the distal surface of the pusher 180. The set distance can be, for example, 2 to 4 mm or 1 to 5 mm. In some embodiments, the set distance can be varied depending on user need and anatomical constraints. A person skilled in the art should understand that the at least one retainer may comprise various structural components configured to removably couple with the cutting device 150. In some embodiments, the at least one retainer may comprise a groove configured to hold the snare loop 154. In some embodiments, the at least one retainer may comprise holes or indents configured to fit with bent or protruding portions of the snare loop 154. A person skilled in the art should also understand that the at least one retainer may be formed on any portion of the pusher 180, for example, the proximal surface, the distal surface, the inward facing surface, or the outward facing surface.

In various embodiments, the pusher 180 can be removably coupled with the snare loop 154 by various means. In some embodiments, the snare loop 154 can be detachably glued to the pusher 180. In some embodiments, the snare loop 154 can be magnetically attached to the pusher 180. In some embodiments, the snare loop 154 can be removably coupled to the pusher 180 by a breakable seal. The breakable seal may comprise a rigid seal attached to the pusher 180 and configured to detach from the pusher 180. The breakable seal may also comprise a soft seal attached to the pusher 180, where the snare loop 154 is configured to break the seal by cutting through the soft seal. A person skilled in the art should understand that in various embodiments, when the snare loop 154 is removably coupled with the pusher 180, the snare loop 154 can be positioned at a set distance from the distal surface of the pusher 180, where the set distance can be, for example, 2 to 4 mm or 1 to 5 mm.

Figure 3D:
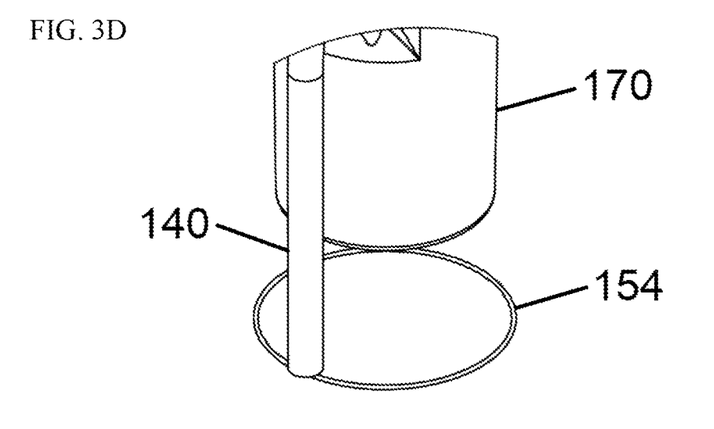
FIG. 3D is a perspective view of a cutting device, a catheter, and an adaptor according to an exemplary embodiment.

The cutting device 150 is an endoscopic tool for resecting tissue, and operates between an open state and a closed state. In some embodiments, as illustrated in FIG. 2B, the cutting device 150 includes the snare drive cable 152 and the snare loop 154. In some embodiments, the snare drive cable 152 and the snare loop 154 are formed with conductive metal wire, which allows the use of diathermic energy by directing electric current in the snare drive cable 152 and the snare loop 154. In some embodiments, the snare drive cable 152 and the snare loop 154 can be formed with materials including stainless steel, nitinol, nickel-titanium shape memory alloy, and polymers such as PTFE, polyolefin, and fluorinated ethylene propylene. In some embodiments, the snare drive cable 152 is attached to the snare loop 154 by welding at an angle substantially perpendicular to the plane defined by the snare loop 154. In some embodiments, as illustrated in FIG. 3D, the snare drive cable 152 extends within the catheter 140. In some embodiments, the proximal end of the snare drive cable 152 is operatively coupled with the handle 130. FIGS. 2B and 3D illustrate the cutting device 150 in the open state. In some embodiments, the handle 130 is configured to retract the snare drive cable 152 with respect to the catheter 140. As result, the snare drive cable 152 pulls a portion or the entirety of the snare loop 154 into the catheter 140, such that the snare loop 154 is contracted toward the closed state having a smaller loop area than the loop area of the open state.

In some embodiments, the cutting device 150 is one integral piece of wire. The cutting device 150 extends within the catheter 140 from the proximal end to the distal end, protrudes out of the distal end of the catheter 140 to form a snare loop, and extends within the catheter 140 back from the distal end to the proximal end. As such, both ends of the cutting device 150 are positioned at the proximal end of the catheter 140, where the catheter 140 is operatively coupled with the handle 130. The handle 130 is configured to actuate the cutting device 150 by retracting one end or both ends of the cutting device 150 with respect to the catheter 140, such that the snare loop 154 is contracted.

In some embodiments, the cutting device 150 is one integral piece of wire. The cutting device 150 extends within the catheter 140, with the proximal end positioned at the proximal end of the catheter 140 and the distal end attached to the distal end of the catheter 140. The handle 130 is configured to actuate the cutting device 150 by retracting the proximal end of the cutting device 150 with respect to the catheter 140, such that the snare loop 154 is contracted.

The cutting device 150 is removably coupled with the pusher 180. In some embodiments, as illustrated in FIG. 3B, the snare loop 154 of the cutting device 150 is retained in the passage 1831 and the passage 1841 defined by the at least one retainer of the pusher 180. In some embodiments, when the snare drive cable 152 is retracted by the handle 130, the snare loop 154 is contracted to escape from the passage 1831 and the passage 1841 through the slit 1832 and the slit 1842 defined by the pusher 180, and move radially inward into the central opening 185 defined by the pusher 180.

A person skilled in the art should understand that the cutting device 150 may comprise any known endoscopic tools for cutting a tissue, as long as the cutting device 150 can be removably coupled with the pusher 180. In some embodiments, the cutting device 150 comprises one or more jaws for cutting a tissue. A person skilled in the art should also understand that the cutting device 150 may be removably coupled to any portion of the pusher 180, for example, the proximal surface, the distal surface, the inward facing surface, or the outward facing surface of the pusher 180. In addition, a person skilled in the art should understand that in any embodiment, the cutting device 150 can be positioned at a set distance from the distal surface of the pusher 180, where the set distance can be, for example, 2 to 4 mm or 1 to 5 mm.

In some embodiments, as illustrated in FIG. 3B, the cutting device 150 is removably coupled to the pusher 180 in the open state. A person skilled in the art should understand that the cutting device 150 may comprise various endoscopic tools allowing the operation between an open state and a closed state. In various embodiments, the cutting device 150 is removably coupled to the pusher 180 in the closed state or an intermediate state between the open state and the closed state.

Figure 3E:
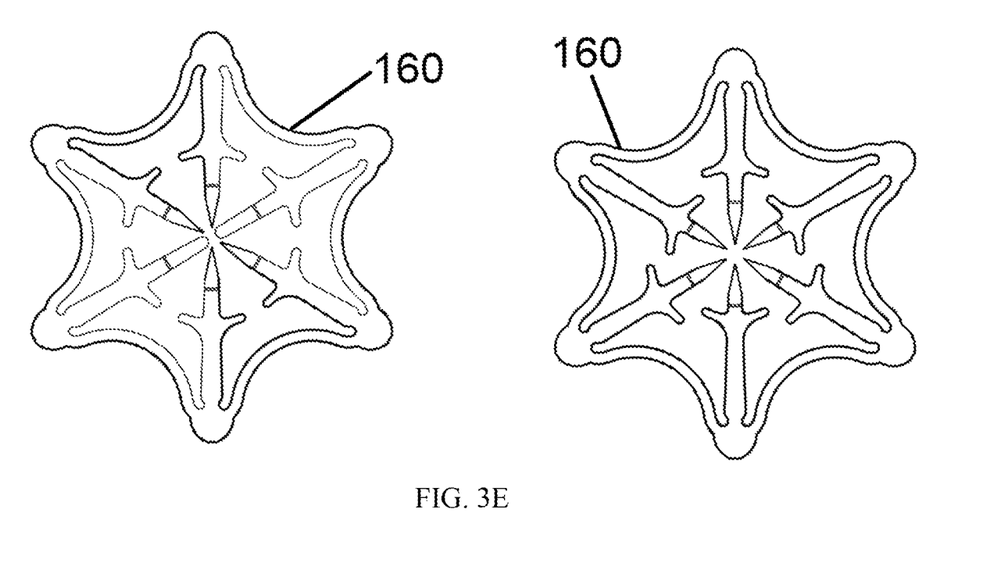
FIG. 3E is an illustration of a clip according to an exemplary embodiment.

The clip 160 is an endoscopic clip which can be deployed to engage onto a tissue. The clip may be based on the Padlock Clip® Defect Closure System currently marketed by STERIS Corporation. In some embodiments, the clip 160 comprises a plurality of tines for engaging the tissue. In some embodiments, each tine of the clip 160 may be blunt or pointed for various purposes, for example, stopping bleeding by compressing the tissue, allowing for optimal healing abilities while still allowing blood flow to the tissue, and holding the tissue together until the site heals itself. FIG. 2B illustrates the clip 160 in the open state, and FIG. 3E illustrates the clip 160 in the closed state. The clip 160 is made from resilient materials which can store strain energy, for example, elastic metal alloy such as nitinol. In some embodiments, the clip 160 can be formed with materials including stainless steel, nitinol, nickel-titanium shape memory alloy, and polymers such as PTFE, polyolefin, and fluorinated ethylene propylene. The clip 160 rests in the closed state when no external force is applied, and can be deformed into the open state by application of external force. When in the open state, the clip 160 defines a central opening 165. When the external force is no longer applied, the clip 160 releases the stored energy and reforms back to the closed state.

Figure 4:
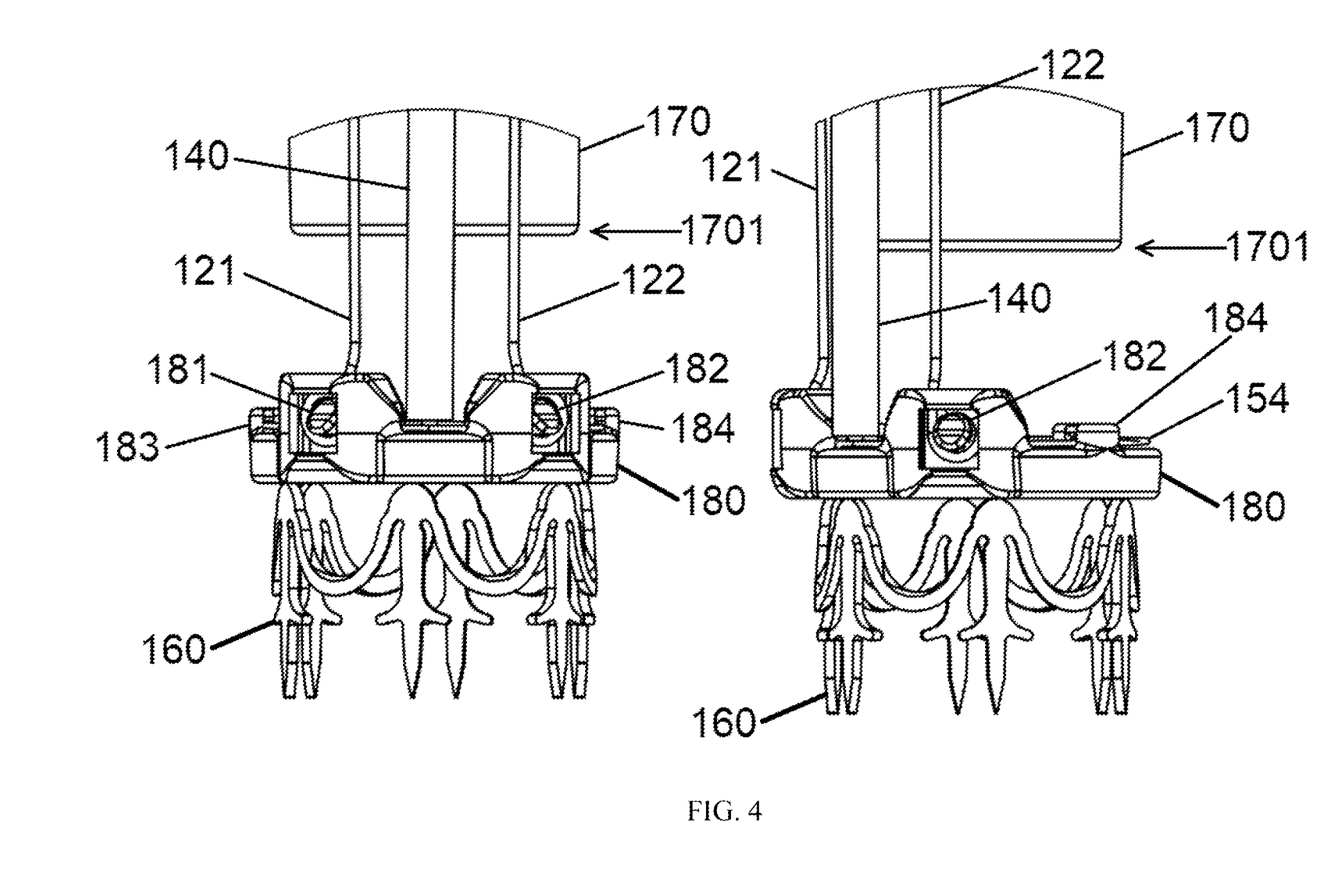
FIG. 4 is an illustration of an adaptor, a clip, and the assembly of a pusher, a cutting device, a first driver, a second driver, and a catheter according to an exemplary embodiment.

FIG. 4 illustrates the assembly of the pusher 180 and the clip 160 onto the adaptor 170. In some embodiments, the pusher 180 is disposed on the adaptor 170 by inserting the adaptor 170 into the central opening 185 defined by the pusher 180. In other words, the pusher 180 rides along the outside surface of the adaptor 170, where the pusher 180 can slide in the axial direction with respect to the adaptor 170. In some embodiments, the at least one driver is attached to the pusher 180 by securing onto the at least one knob of the pusher 180. In some embodiments, the clip 160 is deformed into the open state by external force, and the clip 160 in the open state defines a central opening 165. The clip 160 is then loaded onto the adaptor 170 at a position distal to the pusher 180. In some embodiments, the outside surface of the adaptor 170 supports the clip 160 such that the clip 160 is maintained in the open state, which creates a friction against the sliding of the clip 160 with respect to the adaptor 170 in the axial direction. When a predetermined amount of force is exerted on the clip 160 in the distal direction, the clip 160 overcomes the friction to slide off the distal edge 1701 of the adaptor 170 and detach from the adaptor 170. FIG. 5A illustrates the pusher 180 and the clip 160 assembled onto the adaptor 170 in accordance with some embodiments. In some embodiments, as illustrated in FIG. 5A, the clip 160 contacts the pusher 180 such that the clip 160 can be pushed in the distal direction when the pusher 180 moves in the distal direction.

A person skilled in the art should understand that the clip 160 can be loaded onto the inside surface or the outside surface of the adaptor 170, or onto a support surface formed inside the adaptor 170, as long as the clip 160 can be maintained in the open position and can slide off the distal edge 1701 of the adaptor 170. In some embodiments, the clip 160 and the pusher 180 can be disposed on different surfaces of the adaptor 170, where the adaptor 170 provides one or more longitudinal slits allowing the pusher 180 to contact the clip 160 and push the clip 160 in the distal direction.

In some embodiments, the pusher 180 may not contact and push the clip 160 in the distal direction. Instead, a clip driver such as a drive wire or a pull thread can be configured to move the clip 160 in the distal direction, such that the clip 160 can slide off the distal edge 1701 of the adaptor 170.

In some embodiments, each of the at least one sheath defines a passage for each of the at least one driver. In some embodiments, as illustrated in FIG. 2C, the first driver 121 and the second driver 122 respectively extends within the first sheath 111 and the second sheath 112. The at least one sheath can be reinforced sheaths, such as a spring sheath, formed with various materials including, but not limited to stainless steel, HDPE, PTFE, and nitinol. The at least one sheath may be coated inside or outside to improve the deployment of the device. A heat shrink may be applied over the top of the at least one sheath to increase strength along lengths where the sheath transitions from flexible to stiffer segments of the assembly.

In some embodiments, the proximal end of the at least one sheath can be coupled with the clip deployment handle 190. In some embodiments, the distal end of the at least one sheath is attached to the adaptor 170 by, for example, heat staking, gluing, welding, or overmolding. In some embodiments, as illustrated in FIG. 5A, the first sheath 111 and the second sheath 112 are attached to the adaptor 170 respectively by the overmolding 171 and the overmolding 172. As illustrated in FIG. 2C, the overmolding 171 and the overmolding 172 may be integrally formed with the lumen 173 by one step of overmolding. In some embodiments, each of the at least one sheath can be separately attached to the adaptor 170, either before or after the lumen 173 is formed. A person skilled in the art should understand that the at least one sheath can be attached to any portion of the adaptor 170, such as the inside surface of the adaptor 170, as long as the at least one sheath does not interfere with the operations of the endoscopic device and other components of the endoscopic resection assembly 100. In some embodiments, the at least one sheath may penetrate the adaptor 170, such that the at least one sheath extends through a hole formed on the adaptor 170. In addition, a person skilled in the art should understand that the at least one sheath may not be attached with the adaptor 170. Instead, the at least one sheath may be attached with any component of the endoscopic device or the endoscopic resection assembly 100, as long as the at least one sheath does not interfere with the operations of the endoscopic device and other components of the endoscopic resection assembly 100.

The at least one driver comprises endoscopic tools for pushing the pusher 180 in the distal direction. In some embodiments, as illustrated in FIG. 2C, the at least one driver comprises the first driver 121 and the second driver 122 which are drive wires respectively extending within the first sheath 111 and the second sheath 112. In some embodiments, the proximal end of the at least one driver operatively couples with the clip deployment handle 190. The clip deployment handle 190 is configured to actuate the at least one driver, such that the at least one driver advances with respect to the at least one sheath.

The catheter 140 is a catheter configured for allowing the operation of the cutting device 150 between the open state and the closed state. In some embodiments, the catheter 140 defines a passage for the snare drive cable 152 of the cutting device 150. The catheter 140 can be a sheath formed with various materials including, but not limited to stainless steel, HDPE, PTFE, and nitinol. In some embodiments, the catheter 140 and the at least one sheath, for example the first sheath 111 and the second sheath 112, are contained within the same catheter subassembly, such as in a multilumen catheter sheath. In some embodiments, the proximal end of the catheter 140 is coupled with the handle 130. In some embodiments, as illustrated in FIG. 2C, the catheter 140 is coupled with the adaptor 170 by slip fitting into the lumen 173 of the adaptor 170. A person skilled in the art should understand that the catheter 140 may be coupled to any portion of the adaptor 170, such as the inside surface of the adaptor 170, as long as the catheter 140 does not interfere with the operations of the endoscopic device and other components of the endoscopic resection assembly 100. In some embodiments, the catheter 140 may penetrate the adaptor 170, such that the catheter 140 extends through a hole formed on the adaptor 170. In addition, a person skilled in the art should understand that the catheter 140 can be fixed with the adaptor 170, or be detached from the adaptor 170, as long as the catheter 140 does not interfere with the operations of the endoscopic device and other components of the endoscopic resection assembly 100.

Additionally, a marking device, such as a probe, can be provided in the endoscopic device to outline the perimeter of the target tissue to be resected.

In operation, the endoscopic resection assembly is mounted on an endoscopic device through the adaptor 170 configured to attach with the endoscopic device (e.g., Olympus®, Fujinon®, or Pentax® endoscopes) by, for example, press fitting. The operator guides the endoscope into the GI tract and to the lesion that needs to be resected. The perimeter of the target tissue to be resected can be marked with a marking device, such as a probe, provided in the endoscopic device.

In a next step, the target tissue to be resected is recruited into the tissue chamber channel defined by the adaptor 170. In cases where the target tissue is a lesion, some extra tissue surrounding the lesion in addition to the lesion can be recruited into the adaptor 170, which ensures that the entire lesion can be resected and removed. In some embodiments, an endoscopic grasper is provided in the adaptor 170. In some embodiments, the endoscopic grasper advances out of the adaptor 170, grasps a tissue, and pulls the tissue into the adaptor 170. In some embodiments, tissue can be recruited into the adaptor 170 via suction or by other means and endoscopic tools. When the perimeter of the target tissue is initially marked with a marking device, the marked edges can help the operator in determining whether the target tissue is entirely pulled into the cap.

In a next step, the clip 160 is deployed over the tissue. In some embodiments, the clip deployment handle 190 is actuated to advance the at least one driver with respect to the at least one sheath. In some embodiments, through the attachment of the pusher 180 with the at least one driver, a force is exerted on the pusher 180 in the distal direction. As result, as illustrated in FIGS. 5A-5C, the pusher 180 moves in the distal direction with respect to the adaptor 170. In some embodiments, the clip 160 is loaded on the adaptor 170 at a position distal to the pusher 180 and maintained in the open state. In some embodiments, as the pusher 180 moves in the distal direction, the distal surface of the pusher 180 contacts the clip 160 to exert a force sufficient to overcome the friction between the clip 160 and the adaptor 170. As result, the clip 160 slides against the outside surface of the adaptor 170 in the distal direction. As the clip 160 slides off the distal edge 1701 of the adaptor 170, as illustrated in FIGS. 5B and 5C, the support provided by the outside surface of the adaptor 170 becomes insufficient to maintain the clip 160 in the open state. Due to the energy stored in the clip 160, the clip 160 reforms toward the closed state where the tines of the clip 160 engage onto the tissue recruited into the adaptor 170. In cases where the target tissue is a lesion, the clip 160 may engage onto some extra or marginal tissue surrounding the lesion which ensures that the entire lesion can be resected and removed.

The clip deployment handle 190 may be further actuated to advance the at least one driver, which further moves the pusher 180 in the distal direction. In some embodiments, the clip deployment handle 190 is actuated until the pusher 180 sits directly on top of the clip 160. FIGS. 6A-6D illustrates the clip 160 and the pusher 180 in the deployed position in some embodiments, where the tissue is not shown. As illustrated in FIGS. 6A-6D, in some embodiments, when the pusher 180 is in the deployed position, at least a portion of the pusher 180 is distal to the adapter 170. In other words, in some embodiments, at least a portion of the pusher 180 in the deployed position extends beyond the edge 1701 of the adaptor 170. For example, the pusher 180 in the deployed position may extend beyond the edge 1701 of the adaptor 170 by 0 to 3 cm.

In a next step, the tissue is resected by operating the cutting device 150. In some embodiments, the cutting device 150 is operated from the open state toward the closed state while cutting the tissue. In some embodiments, the cutting device 150 is operated from the closed state toward the open state, and then operated from the open state toward the closed state while cutting the tissue. In some embodiments, the handle 130 is actuated to retract the snare drive cable 152 with respect to the catheter 140, which pulls the snare loop 154 into the catheter 140. As result, the snare loop 154 is contracted such that the cutting device 150 operates from the open state toward the closed state. In some embodiments, the cutting device 150 is removably coupled to the pusher 180 where the snare loop 154 is accommodated in the passage defined by the at least one retainer of the pusher 180. When contracted, the snare loop 154 escapes from the passage through the slit defined by the at least one retainer, and moves radially inward into the central opening 185 defined by the pusher 180. As such, the cutting device 150 is removed from the pusher 180, and the tissue recruited in the adaptor 170 is resected by the snare loop 154 moving radially inward. Diathermic energy may be applied through the snare loop to assist the resection. The amount of tissue that can be resected is affected by the axial distance between the distal end of the pusher 180 and the position on the pusher 180 where the cutting device 150 is coupled. In some embodiments, as illustrated in FIGS. 2D and 3A-3C, the cutting device 150 is coupled to the top surface of the pusher 180. As such, the axial distance between the distal end of the pusher 180 and the position on the pusher 180 where the cutting device 150 is coupled is equivalent to the stack height of the pusher 180, that is, the distance between the top surface and the bottom surface of the pusher 180. In such embodiments, when the pusher 180 has a large stack height, there is a large axial distance between the distal end of the pusher 180 and the position on the pusher 180 where the cutting device 150 is coupled. Therefore, the resection will be shallow, with less tissue being resected by the cutting device 150 and more tissue remaining within the central opening 185 defined by the pusher 180 after resection. In contrast, when the pusher 180 has a small stack height, there is a small axial distance between the distal end of the pusher 180 and the position on the pusher 180 where the cutting device 150 is coupled. Therefore, the resection will be deep, with more tissue being resected by the cutting device 150 and less tissue remaining within the central opening 185 defined by the pusher 180 after resection. In various embodiments, the axial distance between the distal end of the pusher 180 and the position on the pusher 180 where the cutting device 150 is coupled can be varied and adjusted, for example by adjusting the stack height of the pusher 180, in order to ensure there is an appropriate amount of tissue to be resected as well as an appropriate amount of tissue remaining within the central opening 185 defined by the pusher 180 after resection. After resection, some tissue remains at the resection site on the proximal side of the clip 160 due to the axial distance between the clip 160 and the position on the pusher 180 where the cutting device 150 is coupled, which ensures that the clip 160 remains engaged with the tissue to close the defect. In some embodiments, when the snare loop 154 is accommodated in the passages positioned at 1 to 5 mm from the distal surface of the pusher 180, about 1 to 5 mm of tissue will remain on the proximal side of the clip 160 after resection. The endoscopic resection assembly, except for the clip 160, is then removed from the GI tract. In some embodiments, for a less traumatic removal process, the clip deployment handle 190 can be actuated to retract the at least one driver which moves the pusher 180 in the proximal direction and back onto the adaptor 170.

In some embodiments, a spring is coupled to the clip deployment handle 190 or the at least one sheath. The spring can be configured to be compressed or extended when the pusher 180 is in the deployed position, such that the spring exerts a force on the at least one driver in the proximal direction. The clip deployment handle 190 can include a stopper for preventing retraction of the at least one driver with respect to the at least one sheath. The clip deployment handle 190 can be configured to activate the stopper by, for example, deforming the stopper, such that the stopper no longer prevents the proximal movement of the at least one driver. As result, the compressed or extended spring moves the at least one driver in the proximal direction with respect to the at least one sheath, and the at least one driver moves the pusher 180 in the proximal direction and back onto the adaptor 170.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An endoscopic resection assembly, comprising:
    an adapter, configured to couple to an endoscopic device;
    a pusher, disposed on the adaptor;
    at least one driver, configured to move the pusher in a distal direction with respect to the adaptor; and
    a cutting device, removably coupled to the pusher,
    wherein the cutting device is configured to be removed from the pusher when at least a portion of the pusher is distal to the adapter,
    wherein the adaptor is configured to be loaded with a clip, so that the clip is released from the adaptor and engages onto a tissue before the cutting device is removed from the pusher.

2. The endoscopic resection assembly of claim 1, wherein the cutting device comprises a snare drive cable and a snare loop, and wherein the snare loop is contracted when the snare drive cable is activated.

3. The endoscopic resection assembly of claim 2, wherein the pusher comprises at least one retainer, and wherein the snare loop is accommodated in a passage defined by at least one retainer.

4. The endoscopic resection assembly of claim 3, wherein the at least one retainer defines a slit, and wherein the snare loop escapes from the passage through the slit when the snare loop is contracted.

5. The endoscopic resection assembly of claim 1, wherein the cutting device is positioned at a set distance from a distal surface of the pusher.

6. The endoscopic resection assembly of claim 5, wherein the set distance is 1 to 5 mm.

7. The endoscopic resection assembly of claim 1, wherein the pusher is disposed on the outside surface of the adaptor, and the clip is loaded on the outside surface of the adaptor.

8. The endoscopic resection assembly of claim 1, wherein the pusher pushes the clip in a distal direction, so that the clip is released from the adaptor and engages onto a tissue.

9. The endoscopic resection assembly of claim 1, wherein the pusher and the clip are secured together.

10. The endoscopic resection assembly of claim 1, wherein an endoscopic grasper recruits the tissue into the adaptor before the clip engages onto the tissue.

11. The endoscopic resection assembly of claim 1, wherein the at least one driver moves the pusher to a position directly on top of the clip after the clip engages onto the tissue.

12. The endoscopic resection assembly of claim 1, wherein the at least one driver moves the pusher so that the pusher extends beyond an edge of the adaptor by 0 to 3 cm after the clip engages onto the tissue.

13. A method for resecting a tissue, comprising:
    removably coupling a cutting device to a pusher;
    disposing the pusher on an adaptor, wherein the adaptor is configured to couple to an endoscopic device, and wherein the adaptor is configured to be loaded with a clip;
    recruiting the tissue into the adaptor;
    deploying the clip over the tissue, wherein the clip is released from the adaptor and engages onto the tissue;
    resecting the tissue by the cutting device, wherein the cutting device is removed from the pusher and resects the tissue.

* * * * *